US006474817B1

(12) United States Patent
McKinnon et al.

(10) Patent No.: US 6,474,817 B1
(45) Date of Patent: Nov. 5, 2002

(54) METHOD FOR ESTABLISHING FIXATION IN VISUAL FIELD PERIMETRY

(75) Inventors: Stuart J. McKinnon, San Antonio, TX (US); Jeffrey L. Stewart, Greenwich, CT (US)

(73) Assignee: VisionRx, Inc., Elmsford, NY (US)

( * ) Notice: Subject to any disclaimer, the term of this patent is extended or adjusted under 35 U.S.C. 154(b) by 150 days.

(21) Appl. No.: 09/604,571

(22) Filed: Jun. 27, 2000

(51) Int. Cl.⁷ .................................................. A61B 3/02
(52) U.S. Cl. ....................................................... 351/243
(58) Field of Search ................................ 351/201, 203, 351/205, 222, 224, 226, 237, 239, 243, 246

(56) References Cited

U.S. PATENT DOCUMENTS 5,946,075 A  *  8/1999  Horn .......................... 351/246

* cited by examiner

*Primary Examiner*—George Manuel
(74) *Attorney, Agent, or Firm*—J. de La Rosa

(57) ABSTRACT

The present invention provides a method for establishing fixation during computerized visual field perimetry, requiring the subject to fixate on a stationary target for a brief instance as he/she moves a secondary target towards the stationary target. In a preferred embodiment, the subject interactively moves the secondary target in the shape of crosshairs toward the stationary fixation target displayed on a monitor using the operations of a computer mouse. The stationary fixation target has preferably the shape of a small red circle in order to make it readily identifiable by the subject. The computer mouse pointer when contacted attaches itself to the secondary target. The subject then moves his head so that the fixation target is directly in front of him/her, and, while staring at the fixation target, moves the secondary target towards the stationary fixation target. When the secondary target overlaps the stationary fixation target, it disappears, causing a flashing visual test stimulus to be displayed to the subject for a preset time. The flashing visual test stimulus appears substantially simultaneous with the overlapping of the secondary target and the fixation target.

21 Claims, 4 Drawing Sheets

METHOD FOR ESTABLISHING FIXATION IN VISUAL FIELD PERIMETRY

CROSS-REFERENCE TO RELATED APPLICATION

This application is related to co-pending application U.S. Ser. No. 09/425,065, entitled "Interactive Method and System For Attracting and Targeting Prospective Clients In The Medical Care Field," filed Oct. 21, 1999, which is incorporated herein by reference.

TECHNICAL FIELD

The present invention relates to a method for measuring a person's field of vision and, more particularly, to a method for establishing fixation during computerized visual field perimetry such as, for example, where conducted over an Internet website.

BACKGROUND OF THE INVENTION

In above identified co-pending application, an interactive method and system is disclosed for medical care providers, namely eye care providers, to more effectively target and attract prospective clients by, among other things, affording them eye examinations over an Internet website. To conduct such an examination, stimuli of different shape, size, speed, frequency, location, color, contrast and/or intensity are displayed on the user's display monitor. Use of such stimuli affords, for example, a convenient manner for conducting computerized visual field perimetry, among other visual tests. A loss of peripheral vision is typically associated with glaucoma, cerebrovascular disease, and pituitary tumors.

In visual field perimetry, the subject's eye is typically fixated on a stationary target (a "fixation point") while visual test stimuli are displayed momentarily within the subject's visual field. The subject's visual field is then mapped by recording his/her response to each visual test stimulus. To reduce eye fatigue, however, various methods have been developed which use instead a moving fixation point. With respect to such a moving fixation point, selected patents as discussed herein below are of interest, and are incorporated herein by reference.

In U.S. Pat. No. 4,995,717, a fixation point is moved around a computer screen while the subject attempts to track its movement by means of a computer mouse. More particularly, the subject moves the cursor, such as a circle, by means of the mouse to keep the fixation point surrounded by the cursor. Fixation is maintained while the cursor is surrounding the fixation point, allowing test stimuli to then be displayed within the subject's peripheral vision.

In U.S. Pat. No. 5,565,949, a fixation point again is moved around a computer screen, but during its movement it changes shape, for example, from a circle to a square, or vice a versa. After such a change in the fixation point, the subject is required to press a mouse button. Failure to respond to the change indicates a loss of fixation.

In U.S. Pat. No. 5,737,060, a moving fixation point, such as in the shape of an ant, is displayed on two independent screens of virtual reality glasses, which are worn by the subject. The fixation point is moved around the display screen of the glasses, with its overall direction of movement being clockwise. Two methods of monitoring fixation are used. In one, the subject must respond to changes in the direction of the fixation point though the use of a computer mouse. Any change in direction which the subject does not respond to is considered a loss of fixation. In the second method, blindspot monitoring is used as the fixation control. In this latter case, a target is displayed in the subject's blindspot on one of the display screens, while the fixation point is displayed on the other screen. If the subject responds to the blindspot target, then there is a loss of fixation since the blindspot target should not have been seen. Otherwise, it is assumed that fixation has been maintained.

Although computerized visual field perimetry systems satisfactorily employ fixation methods, whether stationary or moving, as discussed above herein, it would be desirable to have a method and system for establishing fixation which is less complicated.

SUMMARY OF THE INVENTION

The present invention provides a method for establishing fixation during computerized visual field perimetry, requiring the subject to fixate on a stationary target for a brief instance as he/she moves a secondary target towards the stationary target.

In a preferred embodiment, the subject interactively moves the secondary target, for example, in the shape of crosshairs, toward the stationary fixation target displayed on a monitor using the operations of a computer mouse. The stationary fixation target has preferably the shape of a small red circle in order to make it readily identifiable by the subject. The computer mouse pointer when contacted attaches itself to the secondary target. The subject then moves his head so that the fixation target is directly in front of him/her, and, while staring at the fixation target, moves the secondary target towards the stationary fixation target. When the secondary target overlaps the stationary fixation target, it disappears, causing a flashing visual test stimulus to be displayed to the subject for a preset time.

The flashing visual test stimulus appears substantially simultaneous with the overlapping of the secondary target and the fixation target. Fixation is maintained inasmuch as it is unlikely that the subject can cause the overlapping of the crosshairs and the fixation target if he/she is looking away from the fixation target. Once fixation has been established, the subject's eye is unlikely to wander before the flashing test stimulus is displayed, given that the overlapping and display are almost simultaneous.

As in the conventional perimetry, if the subject observes the flashing visual test stimulus, he/she clicks on one of the mouse buttons, and, afer a slight pause, the secondary target and fixation target reappear on the monitor, preferably at randomly selected positions. Once fixation is again established, the flashing visual test stimulus is displayed at another point within the patient's visual field, until displayed at all preprogrammed locations determined by the type of visual field perimetry performed.

BRIEF DESCRIPTION OF THE DRAWINGS

The features and advantages of the present invention will become more readily apparent from the following detailed description of the invention in which like elements are labeled similarly and in which.

DETAILED DESCRIPTION

Figure 1:
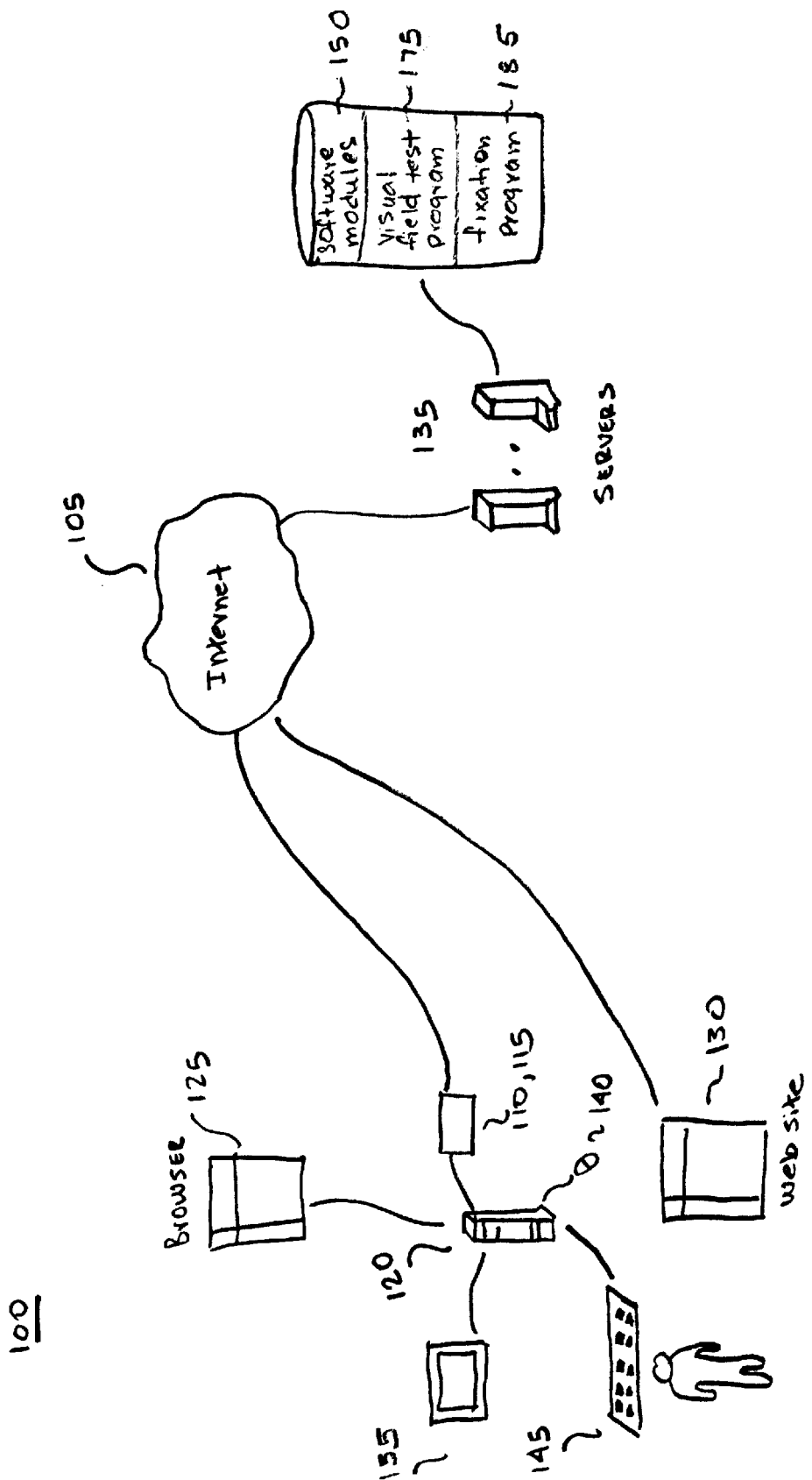
FIG. 1 is a schematic block diagram of an integrated telecommunication system capable of conducting a computerized visual field perimetry, among other visual tests, over the Internet, useful for illustrating the present method of establishing fixation.

The present invention is directed to a method for establishing fixation during computerized visual field perimetry, particularly useful when conducted over an Internet website, as embodied in the system of FIG. 1, and referred herein to as the "Vision Rx system." Although the present invention is embodied for use with the Vision Rx system, it should be clearly understood, that the present invention is also applicable for use with other computerized systems adapted to assess a subject's visual field.

Referring to FIG. 1, there is shown—in schematic block diagram—the Vision Rx system 100, including an integrated telecommunication network 105, such as the Internet. Users connect to the Vision Rx system 100 through the use of a modem 110 or network interface card 115 installed in their personal computer 120. Any standard browser 125, such as the Netscape Navigator or Microsoft Internet Explorer, can be used to remotely access Vision Rx website 130 established by Vision Rx server(s) 135. Website 130 preferably includes the use of text, digital images, audio and/or video, developed using conventional software tools and languages, such as $C^{++}$, Java, ActiveX technology and/or HTML, among others.

To effect user interaction, a user input device, such as a computer mouse 140, or keyboard 145 can be used, to respond to observed visual test stimuli. Various computerized eye examinations are provided to the user using web browser 125, including, for example, unaided visual acuity tests; corrected visual acuity tests; contrast sensitivity tests; color vision tests; visual field tests; and neurologic tests, among others. Such computerized eye examinations can be readily stored as portable software modules 150, such as Java applets, and then downloaded and executed locally on user's personal computer 120, or, alternatively, executed on a computer or computers located at a central facility. Each Vision Rx software module 150 tests for a desired visual deficiency by displaying to the user visual test stimuli of different shape, size, speed, frequency, location, color, contrast, and/or intensity on a display monitor 155, and then by recording and comparing what the user reports seeing with what is presented by computer 120.

Figure 2:
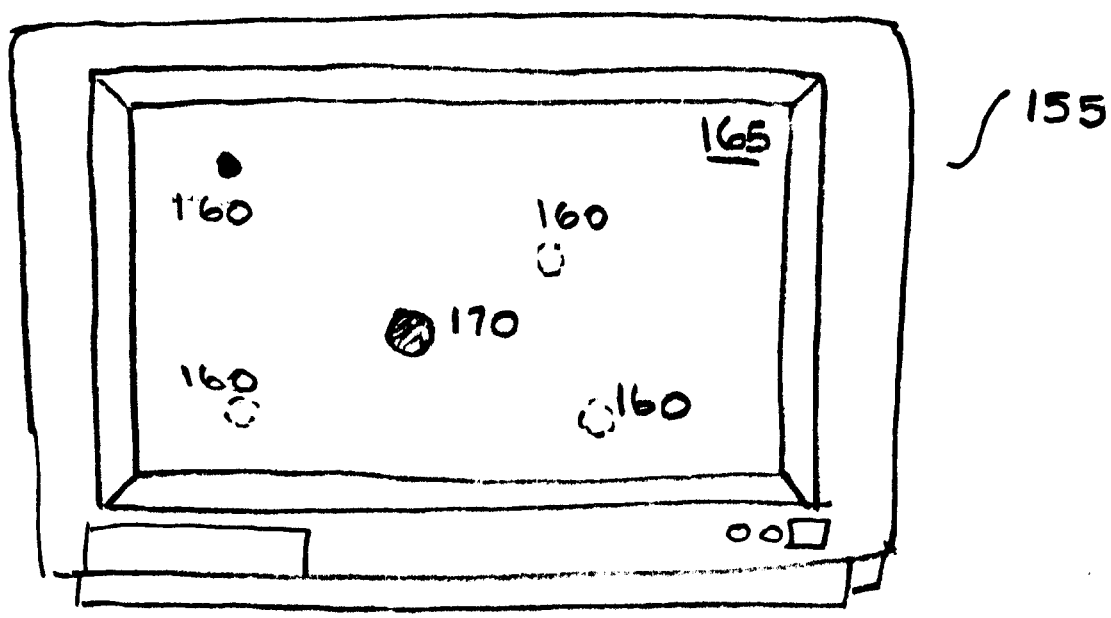
FIG. 2 is an enlarged depiction of the display monitor of FIG. 1 with an exemplary fixation target and visual test stimuli.

As illustrated in FIG. 2, visual test stimuli 160 are represented by pixels and are sent from a video controller (not shown) within computer 120 to display monitor 155 having a viewable area 165 representing the surface where the pixels are output. In addition to displaying visual test stimuli 160, computer 120 monitors the patient's response which is entered by, preferably, clicking a button on computer mouse 140, or alternatively entered using keyboard 145.

For example, with the subject's eye fixated, it is possible to conduct computerized visual field perimetry so as to assess a patient's visual field. More specifically, the perimeter corresponding to viewable area 165 is provided with a fixation point 170 along with visual test stimuli 160 displayed at preprogrammed locations within the subject's visual field, i.e., viewable area 165. Computer 120 records the subject's response to visual test stimuli 160 so as to map the patient's visual field, and may adjust the intensity levels of visual test stimuli 160 to determine precisely the threshold levels at which the stimuli are observed. From the resulting analysis of the visual field mapping, an ophthalmologist is able to recognize any abnormalities in the subject's eye.

Each visual test stimulus 160 can have at least five test attributes, which can be programmed: shape, intensity, size, color, and duration. Likewise, fixation point 170 can have a different shape, intensity, size, and color. The display format of visual test stimuli 160 and fixation point 170 is controlled by the graphical user interface (GUI) of the operating system, such as the Microsoft Windows 95 operating system.

Preferably, the subject views display monitor 155 at a predetermined distance (e.g., 16") such that each visual test stimulus 160 subtends a predetermined angle, but of sufficient distance to test at least the central 30 degrees of the subject's visual field. Of course, the subject views visual test stimuli 160 monocularly, with each eye tested separately. The locations of visual test stimuli 160 within the visual field are chosen to suit different testing requirements.

Software to implement the above described visual field perimetry therefore may include fixating the subject's eye, displaying and varying the location and intensity of visual test stimuli 160, recording the patient's response to the stimuli, and mapping the visual field on the basis of the patient's responses. Such software is readily capable of implementation by those skilled in the art who have been equipped with the understanding of the operation of visual field perimetry, and may be written in $C^{++}$, or any other programming language. Of course, the test data for each subject can be displayed either in graphical or text format on display monitor 155, and/or saved on a hard disk, recalled for later use, imported into a database for statistical analysis, and/or transmitted to another remote location.

As noted above herein, in visual field perimetry, the subject's eye is typically fixated on a stationary target (a "fixation point"), while visual test stimuli are displayed within the subject's visual field. The subject's visual field is then mapped by recording the person's response to each visual test stimulus. To reduce eye fatigue, various methods have been developed which, however, use a moving fixation point. This typically requires that the computer mouse be moved continuously during testing, as discussed herein above, which is difficult for some people, such as the disabled or elderly. As indicated, it would be desirable to have an alternative method for establishing fixation that is less complicated than the prior art.

Incorporated into software modules 150 is a visual field test program 175 for assessing the subject's ability to see visual test stimuli in his/her field of vision. When computerized visual field perimetry is to be performed, the operating system executes visual field test program 175, which for screening purposed may be rudimentary. Prior to conducting this visual field test, a calibration program, however, is executed to determine the physical pixel size of display monitor 155. This is so, because when conducting the visual field test, stimuli of a known dimension or size must be displayed to the subject. Display monitors are, however, not of the same size, varying, for example, from 13" to 21". Thus, without calibration, stimuli of the same pixel size are of a different physical size.

Preferably, the pixel calibration is performed on the basis of the pixel size of a calibration window displayed to the subject with respect to an external object of known dimensions provided by the user, such as a 3.5" diskette, CD jewel case or dollar bill. This calibration method is disclosed in co-pending application, filed on even date herewith, entitled "Method of Calibrating The Physical Pixel Size of A Display Monitor," which is incorporated herein by reference. Of course, other means for calibrating the pixel size known in the art may be used.

To obtain a mapping of the patient's visual field or peripheral vision, the patient's central vision should be fixated while visual test stimuli are displayed in a random fashion at different locations within the patient's visual field. However, the visual test stimuli should be displayed once it is established that the subject's eye is fixated. The present invention affords a method for readily establishing fixation, which requires the subject to fixate on a stationary target for a brief instance as he/she moves a secondary target towards the stationary target, as discussed herein below.

Figure 3:
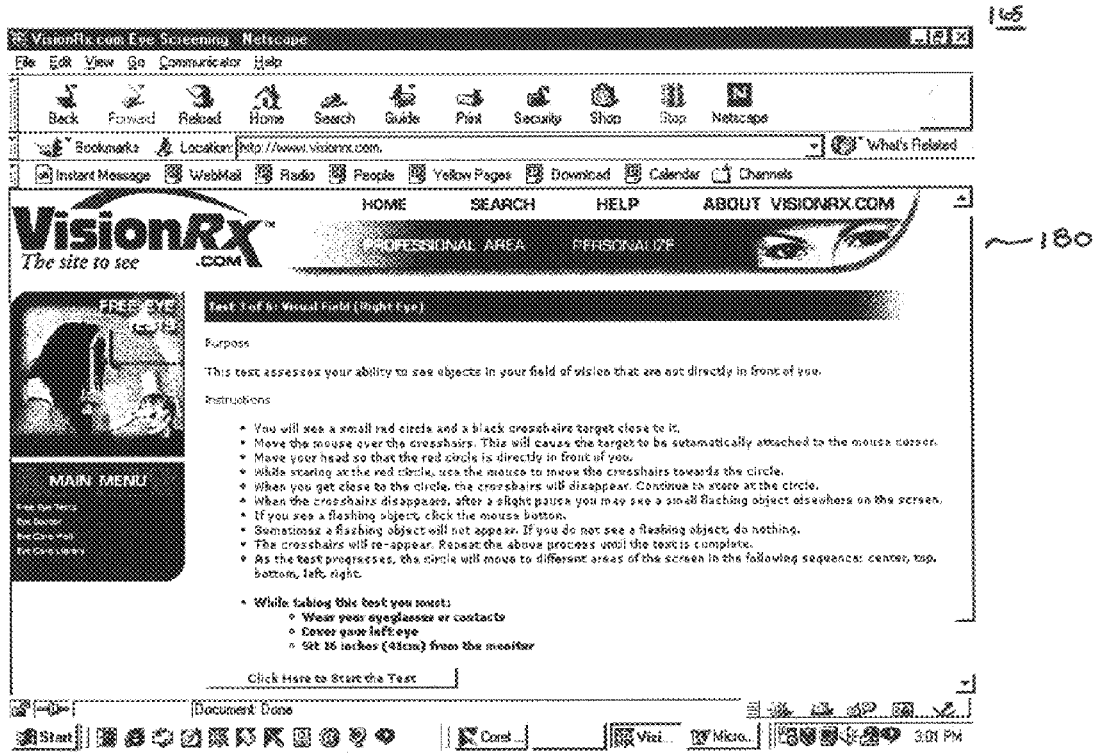
FIG. 3 is an exemplary depiction of the primary window associated with the visual field test program of the present invention.

Computer 120 is understood to execute visual field test program 175 so as to provide a primary window 180 within viewable area 165 in which information associated therewith is displayed and which window is operative to receive commands, such as by pointing, clicking, or selecting. This window mechanism is readily employed in programs running under Microsoft Windows operating system available from Microsoft Corporation, Redmond, Wash. A similar X-windows mechanism is also available in the Macintosh operating system available from Apple Computer, Inc. Shown in FIG. 3 is primary window 180 accessed through website 130, which contains the title, menu bar and tool bars related to the window, along with instructions informing the subject on how to take the visual field test. Preferably, primary window 180 is the full size of viewable area 165, and, for a VGA display under Windows 95, is 1024 pixels horizontally by 768 pixels vertically.

Figure 4:
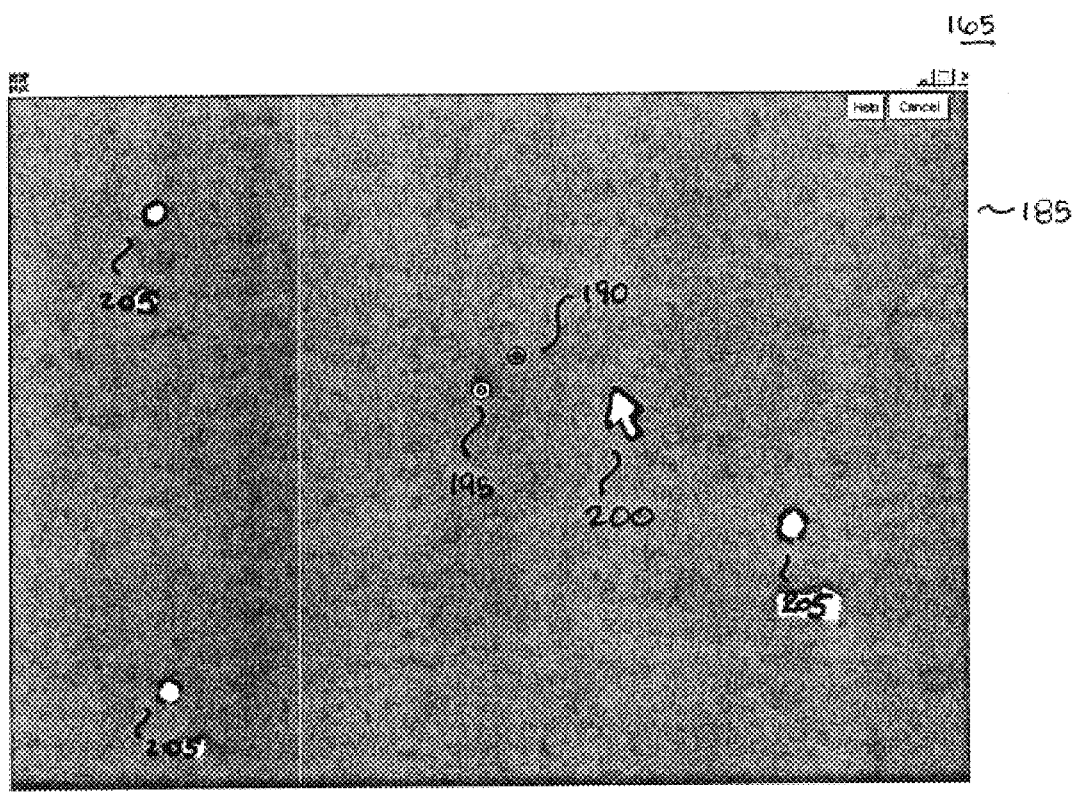
FIG. 4 is an exemplary depiction of a visual field window associated with the fixation program of the present invention.

Referring to primary window 180, once the subject has read the instructions, the user then clicks on the box labeled Click Here to Start the Test, which then causes a visual field window 185 to be displayed, as illustrated in FIG. 4. Associated with visual field window 185 is a fixation program 185 which allows the subject to interactively move a secondary target 190 in the shape of, for example, crosshairs toward a stationary fixation target 195 using the operations of computer mouse 140. Stationary fixation target 195 has the shape of a small red circle in order to make it readily identifiable by the subject. This red circle has a radius typically from about 1 to tens of pixels, so as to subtend about 1–2 degrees.

In accordance with the principles of the invention, pointer 200 associated with computer mouse 140 is moved by the subject towards the secondary target 190, which when contacted attaches itself to secondary target 190. The subject then moves his head so that the red circle (fixation target 195) is directly in front of him/her, and, while staring at the red circle, moves the crosshairs (secondary target 190) towards stationary fixation point 195 (red circle). The movement of the crosshairs (secondary target 190) is controlled using computer mouse 140. When the crosshairs (secondary target 190) overlaps stationary fixation target 195, it disappears, causing a flashing visual test stimulus 205 to be displayed to the subject for a preset time, typically about ⅕ of a second.

Flashing visual test stimulus 205 appears substantially simultaneous with the overlapping of secondary target 190 and fixation target 195. Fixation is maintained inasmuch as it is unlikely that the subject can cause the overlapping of the crosshairs (secondary target 190) and fixation target 195 if the he/she is looking away from the fixation target. Once fixation has been established, the subject's eye is unlikely to wander before the flashing test stimulus is displayed given that the overlapping and display are almost simultaneous. The speed at which the subject accomplishes the above task is dependent on the subject's dexterity, but typically takes at most a few seconds.

As in conventional perimetry, if the subject observes flashing visual test stimulus 205, he/she clicks on one of the mouse buttons, and, afer a slight pause, secondary target 190 and fixation target 195 reappear, preferably at randomly selected positions on viewable area 165. Preferably, fixation target 195 appears on different areas of the display monitor in the following sequence: center, top, bottom, left and right. Moreover, with viewable area 165 broken into four quadrants, fixation target 195 can be moved into the outer corner of each of the four quadrants to access peripheral points in the patient's visual field. Once fixation, however, is again established, flashing visual test stimulus 205 is displayed at another point within the patient's visual field, until displayed at all preprogrammed locations determined by the type of visual field perimetry performed.

If the subject fails to respond to visual test stimulus 205 within a preset time, it is recorded as "missed." If the button is pressed when no visual test stimulus is displayed, this is assumed to be an illegal response, caused, for example, by the subject's lack of attention. Missed stimuli, if desired, can be retested at the same size to verify that the subject is unable to visualize the stimuli or retested at a larger size to assess the depth of the visual defect. The duration between successive visual test stimuli is determined by the subject's dexterity in moving secondary target 190 towards fixation target 195, allowing each subject to proceed at his/her own pace. Note, however, that the sensitivity of the visual field test can be adjusted by selecting the radius of flashing visual test stimuli 205, typically subtending from about 0.1 to 1.5 degrees.

Using accepted standards of automated perimetry, it is preferable to display visual test stimuli 200 at each of the 54 grid points of the standard 24-2 test pattern, wherein each grid point is spaced about 6 degrees of visual field. The number of stimuli, their locations and the difference in intensity levels, however, may be chosen in a different manner, depending on the test strategy that is to be employed. For example, a rudimentary visual field screening can be performed with about six visual test stimuli. Also, a "binary staircase" or "supra threshold" testing strategy can be used, depending on the number of visual field locations to be used and the desired test time.

Also, to ensure reliability in the patient's response, false-positive and false-negative visual test stimuli may be presented to the subject, such techniques being well known to those skilled in the art. In the former case, a blank stimulus is displayed, whereas in the latter a stimulus is displayed having an intensity higher than the one previously displayed at the same visual field location.

Accordingly, the present invention provides a method for establishing fixation, particularly useful when conducting computerized visual field perimetry over an Internet website. Although, the method is embodied in a system employing the World Wide Web, the present fixation method is also equally applicable for use in computerized visual field perimetry conducted on stand alone personal computers. As such, the embodiment discussed herein above is merely illustrative of the principles of the invention. Various modifications will become apparent to those skilled in the art from the foregoing description and accompanying figures.

Such modifications are intended to fall within the scope of appended claims.

What is claimed is:

1. A method for establishing fixation in a visual field perimeter, comprising the steps of:

displaying to a subject a stationary fixation target, and a secondary target which is movable by the user;

requiring the user to move the secondary target until the secondary target overlaps the stationary fixation target;

on the overlapping of the secondary target with the stationary fixation target, flashing a visual test stimulus to the user at a predetermined location within the user's field of vision.

2. The method of claim 1 further wherein the stationary fixation target is displayed at peripheral points in the user's field of vision.

3. The method of claim 1 further comprising the steps of displaying a cursor to the user, and requiring the user, prior to being able to move the secondary target, to move the cursor until it contacts and then attaches itself to the secondary target.

4. The method of claim 1 wherein the visual test stimulus is displayed to the user substantially simultaneous with the overlapping of the stationary fixation and the secondary targets.

5. The method of claim 1 further comprising the step of displaying information on the operations of the visual field perimetry within an active window of an application program.

6. The method of claim 1 further comprising the step of establishing an active window of an application program for receiving user commands through a user input device for moving the cursor and the secondary target.

7. The method of claim 1 wherein the stationary fixation target is a red circle.

8. The method of claim 1 wherein the secondary target is in the shape of crosshairs.

9. The method of claim 1 further comprising the step of recording whether the user observes the visual test stimulus.

10. The method claim 1 further comprising the step of varying the size, shape, intensity, and/or color of the stationary fixation target.

11. In a visual field perimeter having a computer, a user input device, and a display monitor with a viewable area representing the surface where visual test stimuli are displayed to the user, a method for establishing fixation, comprising the steps of:

displaying a stationary fixation target within a region of the viewable area;

displaying a cursor and secondary target within other regions of the viewable area;

requiring the user to move the cursor towards the secondary target until the cursor contacts and then attaches to the secondary target, using commands received through the user input device; and as the user stares at the stationary fixation target, requiring the user to move the secondary target towards the stationary fixation target until overlapping with the stationary fixation target, using commands received through the user input device; and displaying visual test stimuli to the user substantially simultaneous with the overlapping of the stationary fixation and the secondary targets.

12. The method of claim 11 wherein the stationary fixation target is displayed at peripheral points in said viewable area.

13. The method of claim 11 wherein said viewable area comprises an active window of an application program for displaying information on the operations of the visual field perimetry.

14. The method of claim 11 wherein said viewable area comprises an active window of an application program for receiving user commands through the user input device for moving the cursor and the secondary target.

15. The method of claim 11 wherein the stationary fixation target is a red circle.

16. The method of claim 11 wherein the secondary target is in the shape of crosshairs.

17. The method of claim 11 wherein the user input device is a computer mouse.

18. The method of claim 11 further comprising the step of recording whether the user observes the visual test stimuli.

19. The method claim 11 further comprising the step of varying the size, shape, intensity, and/or color of the stationary fixation target.

20. The method of claim 11 further comprising the step of displaying the visual test stimuli at known locations with respect to the stationary fixation target.

21. The method claim 11 wherein the steps of displaying and moving are conducted over the Internet.

* * * * *